United States Patent [19]

Elias et al.

[11] Patent Number: 5,549,566
[45] Date of Patent: Aug. 27, 1996

[54] VALVED INTRAVENOUS FLUID LINE INFUSION DEVICE

[75] Inventors: Allen M. Elias, Mundelein; Warren P. Frederick, Wonder Lake; David E. Kramer, Northbrook, all of Ill.

[73] Assignee: Abbott Laboratories, Abbott Park, Ill.

[21] Appl. No.: 330,284

[22] Filed: Oct. 27, 1994

[51] Int. Cl.[6] .................................................. A61M 39/26
[52] U.S. Cl. ........................................... 604/167; 604/169
[58] Field of Search .................................. 604/167, 169, 604/256

[56] References Cited

U.S. PATENT DOCUMENTS

| | | | |
|---|---|---|---|
| 4,496,348 | 1/1985 | Genese et al. | 604/169 |
| 4,512,766 | 4/1985 | Vaillancourt | 604/169 |
| 4,917,668 | 4/1990 | Haindl | 604/169 |
| 4,966,588 | 10/1990 | Rayman et al. | 604/167 |
| 4,998,927 | 3/1991 | Vaillancourt . | |
| 5,108,380 | 4/1992 | Herlitze et al. | 604/169 |
| 5,195,980 | 3/1993 | Catlin | 604/256 |
| 5,211,634 | 5/1993 | Vaillancourt | 604/256 |
| 5,234,410 | 8/1993 | Graham et al. | 604/167 |
| 5,300,034 | 8/1993 | Behnke et al. | 604/167 |
| 5,330,435 | 7/1994 | Vaillancourt | 604/167 |

*Primary Examiner*—Paul J. Hirsch
*Attorney, Agent, or Firm*—A. Nicholas Trausch; Brian R. Woodworth

[57] ABSTRACT

A valve including a substantially rigid cannula and a valve member connected for operable communication with the cannula. The valve member is formed from a substantially resilient material and is movable with respect to the cannula between a first closed position and a second open position. The cannula cooperates to extend through the valve member during movement from the first closed position to the second open position to establish a fluid flow path through the cannula and the valve member. A sealing member is also provided which operates independent from a flow of fluid within the fluid flow path and independent from any component utilized with the valve to automatically provide positive sealing of an opening within the valve member when the valve member is positioned in the first closed position, the cannula extending through the opening during movement of the valve member.

19 Claims, 3 Drawing Sheets

5,549,566

VALVED INTRAVENOUS FLUID LINE INFUSION DEVICE

TECHNICAL FIELD

The present invention relates generally to vaned, intravenous fluid line infusers, and more particularly to a vaned infuser in the form of a connector or adaptor that includes a luer activated mechanical valve and attaches two medical implements or components, such as a syringe and a female luer adaptor of an intravenous fluid line, to provide a flow of fluid for parenteral administration from the syringe to the female luer where the valve prevents fluid flow before assembly of the connector, enables attachment of the components and subsequent fluid flow therebetween and automatically provides a positive seal, independent of the fluid flow and a connector housing, upon disassembly of the components.

BACKGROUND OF THE INVENTION

In parenteral administration of fluids, a number of medical implements or components typically are readily interconnected at the point of administration to provide a flow of the desired fluid or medicament from a container, such as a syringe, vial or the like, to a patient. Such components typically include various connectors, adaptors, vanes and fluid lines.

For example, a syringe or other container typically is connected to a drug administration set, such as an intravenous fluid line or I.V., to dispense the syringe fluid or medicament into the I.V. set. The I.V. set in turn is connected to a venipuncture device for administration of the fluid or medicament into the blood stream of a patient.

To connect the syringe to the I.V. set, a connector or adaptor is utilized which typically is first secured to the syringe and then to a port or connector of the I.V. set. Upon assembly of the syringe to the connector, a vane within the connector typically is activated to enable flow of fluid or medicament out of the syringe, through the connector and into the I.V. set.

An example of such an adaptor is disclosed in International Application No. PCT/US92/10367 (International Publication No. WO 93/11828) which provides a medical valve having a reusable seal cap, with or without a precut slit, that may be repeatedly pierced by a sharp pointed tip of a spike contained within the valve. To reseal the aperture formed by the spike or the precut slit within the seal cap after disconnection of the medical valve, the seal cap includes an integrally formed pressure responsive member and associated annular space.

The annular space is filled with fluid under pressure, such as the blood pressure of a patient to which the medical valve is attached. The fluid presses against the pressure responsive member to close the aperture or precut slit.

Such a resealing feature, however, depends on a flow of fluid under pressure which is not available in many applications. Additionally, even when such fluid pressure exits, sealing of the seal cap frequently is inadequate, which can cause leakage and possible contamination.

It therefore would be desirable to provide a valve for use with a medical component, such as an infuser, adaptor or connector, that can be utilized to establish a flow of fluid or medicament between two components of a parenteral fluid delivery system and provides an automatic, positive seal, independent of the fluid flow or a housing of the connector, upon disassembly of the components to prevent leakage and reduce contamination.

SUMMARY OF THE INVENTION

The invention provides a valve for use within a housing of a medical component, such as a connector or adaptor of a parenteral fluid delivery system. The valve includes a substantially rigid cannula mounted within the housing and a valve member positioned within the housing for operable communication with the cannula.

The valve member is formed from a substantially resilient material and is movable within the housing between a first closed position and a second open position. The cannula cooperates to extend through the valve member during movement of the valve member from the first closed position to the second open position to establish a fluid flow path through the cannula and the valve member.

A sealing member is also provided which is independent from both a flow of fluid within the fluid flow path and the housing and automatically provides positive sealing of an opening within the valve member when the valve member is positioned in the first closed position. The cannula extends through the opening during movement of the valve member.

The cannula can be blunt, in which case a preformed slit is provided through the valve member to form the opening. Alternatively, the cannula can be pointed and forms the opening through the valve member.

In either event, a spring bias is provided between the valve member and the housing for maintaining the valve member in the first closed position when not in use and for automatically returning the valve member to the first closed position from the second open position upon disassembly of the valve member from another component or fluid delivery system. The spring bias can be provided by the valve member itself or by a separate spring member.

In a preferred form of the invention, the sealing member is provided as a band or ring positioned about a portion of the valve member having the opening. The band or ring provides a positive mechanical reinforcement to that portion of the valve member and allows for passage of the cannula through the opening while providing a leak-proof seal to the opening upon removal of the cannula.

The valve member preferably includes a portion thereof for activation by a male luer member for providing movement between the first and second positions, where the portion is accessible from an exterior of the housing for cleaning before and after use to maintain aseptic conditions. The housing typically is formed as a connector or adaptor having connecting portions for attachment between the desired medical components.

Numerous other advantages and features of the present invention will become readily apparent from the following description of the invention, the claims and the accompanying drawings.

DESCRIPTION OF THE PREFERRED EMBODIMENTS

While this invention is susceptible of embodiment in many different forms, the specification and the accompanying drawings disclose one or more forms as examples of the invention. The invention is not intended to be limited to the embodiments described, the scope of the invention being pointed out in the appended claims.

For ease of description, the device of this invention is described in a typical operating position and terms such as upper, lower, horizontal etc. are utilized with reference to this position. It will be understood, however, that the device of this invention may be manufactured, stored, transported, and sold in an orientation other than the position described.

Some of the figures illustrating the embodiments of the device of the present invention show conventional components, structural details and mechanical elements that will be recognized by one skilled in the art. The detailed descriptions of such elements, however, are not necessary to an understanding of the invention and, accordingly, are not presented herein.

Figure 1:
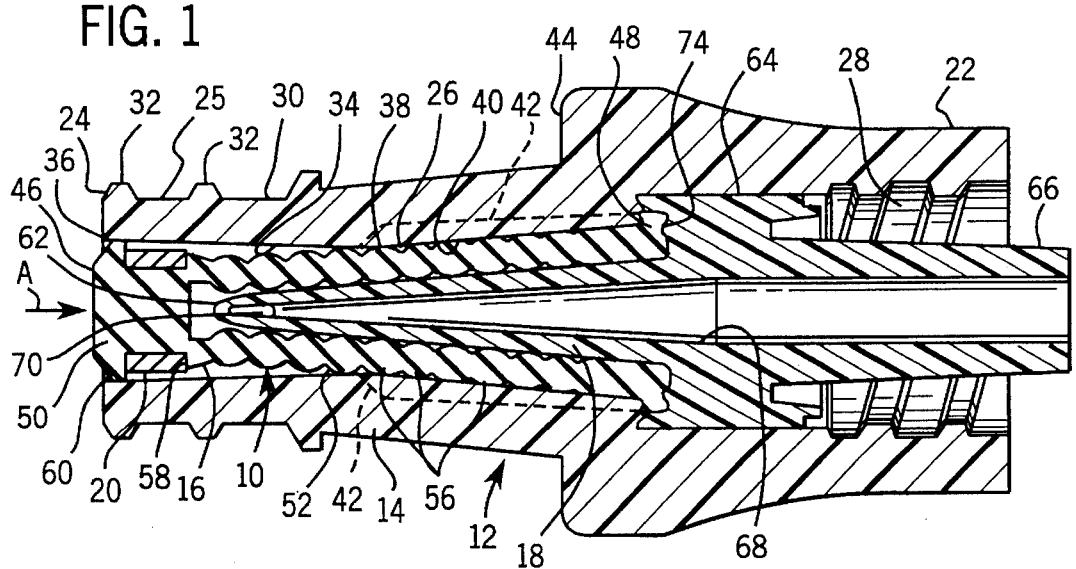
FIG. 1 is a longitudinal cross-sectional view of an embodiment of a valve of the invention illustrated in its closed position within a housing of a medical component for use with a pointed cannula.

Referring to FIG. 1, an embodiment of the valve of the invention is generally designated by the reference numeral 10. The valve 10 is illustrated for use within a medical component of a fluid or medicament delivery system, such as an infuser, connector or adaptor 12. It is to be understood, however, that the valve 10 can be utilized with a variety of components without departing from the teachings of the present invention.

The valve 10 is preferably secured within a housing 14 of the connector 12 and substantially includes a valve or stopper member 16, a cannula 18 and a compression or reinforcement band or ring 20. Although the connector 12 is preferably designed as a one-way fluid connector for flow of fluid or medicament from the left to right with respect to FIG. 1, it is to be understood that the direction of fluid flow as well as the particular details, size and shape of the connector 12 can vary, including providing for two-way fluid flow, if desired.

Figure 2:
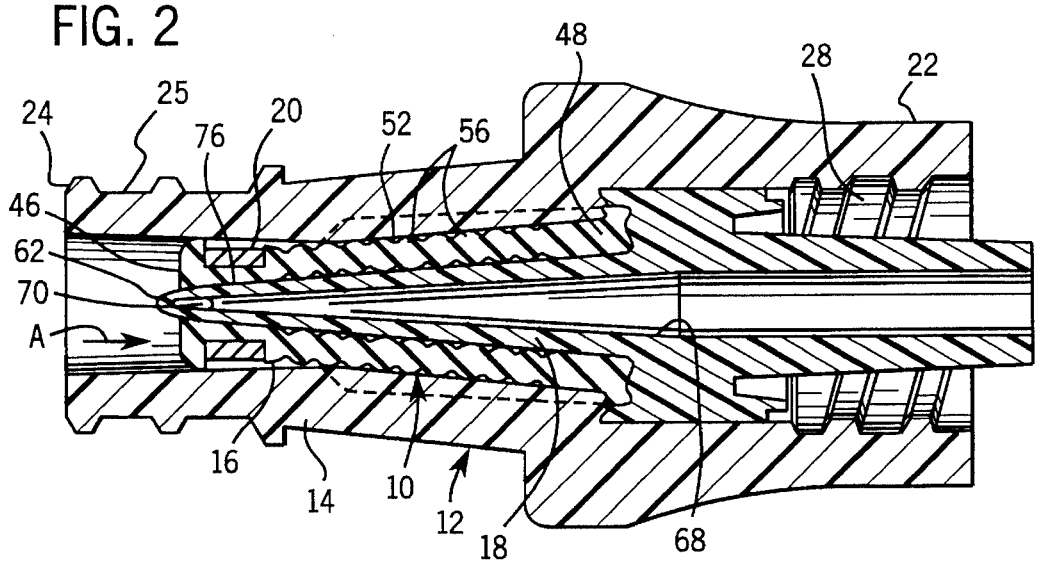
FIG. 2 is a longitudinal cross-sectional view of the valve and housing of FIG. 1 illustrating the valve in its open position.

Briefly, in operation, upon connection of a male tipped luer syringe (not illustrated) to a second end 24 of the housing 14, the valve member 16 is moved in the direction of arrow "A" from a first closed position, illustrated in FIG. 1, to a second open position illustrated in FIG. 2. During such movement, the valve member 16 is longitudinally compressed by the male luer providing a longitudinal spring bias between the valve member 16 and the housing 14. Additionally, the cannula 18 pierces the valve member 16 forming an opening therethrough to enable fluid flow from the syringe connected to the second end 24 to the first opposite end 22 of the housing 14.

As the cannula 18 pierces the valve member 16, the material of the valve member 16 is laterally compressed between the cannula 18 and the ring 20. The lateral compression provides a lateral spring bias within the resilient material of the valve member 16.

Upon disconnection of the male luer from the second end 24, the longitudinal spring bias provided by the longitudinal compression of the valve member 16 automatically returns the valve member 16 to the first closed position. Additionally, the lateral spring bias provided by the compressed material of the valve member 16 between the cannula 18 and the ring 20 is released to provide a positive mechanical seal of the opening thereby preventing fluid flow therethrough, leakage and possible contamination. Details of the structure of the valve 10 and the connector 12 will now be provided.

The housing 14 preferably includes first and second opposite ends 22 and 24 and an internal chamber 26 within which the valve 10 is secured. The first end 22 includes a threaded male connector portion 28 formed therewith for connection to a patient, through I.V. set tubing or the like. The second end 24 of the housing 14 is formed as a female connector portion 25 for accepting the male tipped luer syringe.

It is to be noted that any type of fluid, medicament or blood flow line or vessel can be connected to the female connector portion 25 of the second end 24. For ease of description, the present invention will be described with respect to the male end of a syringe being connected to the female connector portion 25 of the second end 24 and a female luer being connected to the male connector portion 28 of the first end 22 where the female luer is in communication with a parenteral fluid delivery system, such as an I.V. set. The syringe, female luer and I.V. set are omitted from the drawings for brevity.

An exterior surface 30 of the second end 24 of the housing 14 preferably is formed to include one or more ears, threads or similar members 32 for connection of a male luer lock connector or the like. A substantially cylindrical portion 34 of the internal chamber 26 is included with the second end 24 and preferably extends inward from a first outside end 36 to a second inside end 38.

The second inside end 38 of the cylindrical portion 34 communicates with a portion 40 of the chamber 26 which extends the remaining length of the housing 14 to the first end 22. To accommodate portions of the valve member 16 during compression as explained below, the portion 40 flares outward toward the first end 22 and includes a plurality of longitudinal channels 42 radially spaced about its interior surface. To readily grip the connector 12 during use, a shoulder 44 can be formed about an exterior surface of the housing 14.

The valve member 16 is substantially circular in cross section and includes a first end 46 and a second opposite end 48. The second end 48 is connected to a portion of the cannula 18 while the first end 46 either protrudes slightly from or is substantially flush with the second end 24 of the housing 14.

In order to provide the desired sealing, the valve member 16 is preferably formed from a substantially resilient material such as rubber, silicone or the like. The particular material of the valve member 16, however, can vary so long as the valve member 16 functions as described herein.

The valve member 16 is preferably formed from a single piece of resilient material and includes a head portion 50 forming the first end 46 and a main body portion 52 extending between the head portion 50 and the second end 48 of the valve member 16. The main body portion 52 tapers from the second end 48 toward the head portion 50.

A plurality of ribs 56 provide increased flexibility of the valve member 16 and the desired spring bias from compression between ribs 56 in a direction substantially along the length of the main body portion 52. Although ten ribs 56 are illustrated, the particular number of ribs 56 as well as their size and location can vary so long as the valve member 16 functions as described herein.

The head portion 50 includes an annular recess 58 formed about its exterior for seating of the ring 20 therein. The particular size and shape of the recess 58 and ring 20 can vary so long as the desired sealing is provided to the opening of the valve member 16.

To engage the cylindrical portion 34 for proper alignment and sliding movement thereon, the head portion 50 also includes a circumferential lip 60. The lip 60 does not add materially to the sealing abilities of the valve member 16 and can be omitted if desired.

The cannula 18 includes a first pointed end 62, an intermediate portion 64, a second opposite end 66 and an internal passageway 68. The cannula 18 is preferably formed from a substantially rigid plastic and is conical in longitudinal cross-section tapering from the intermediate portion 64 to the first pointed end 62.

The cannula 18 includes one or more openings 70 proximate its first pointed end 62 which preferably are formed along the sides of the cannula 18 to provide flow channels when the first pointed end 62 pierces the valve member 16 as desired. The size and shape of the openings 70 can vary so long as a flow of the desired fluid is provided therethrough when the valve member 16 is positioned in the open position illustrated in FIG. 2.

To connect the second end 48 of the valve member 16 to the intermediate portion 64, a recess 74 is included on a portion of the intermediate portion 64 facing the valve portion 16. The second end 48 of the valve member 16 is preferably secured within the recess 74 by snap engagement but may alternatively be secured by sonic welding or an adhesive, etc.

The end 66 of the cannula 18 is formed as a central tapered engagement column for direct connection to a patient through I.V. set tubing or the like. The particular design of the end 66, however, can vary to accommodate a variety of different medical components.

In operation, the male luer tip of a full syringe without a needle (not illustrated) preferably is connected to the female connector portion 25 on the second end 24 of the housing 14. The female luer of an I.V. line is then connected to the male connector portion 28 of the first end 22 of the housing 14.

If desired, however, the female luer of the I.V. line can be connected first. In either event, the first end 46 of the valve member 16 is preferably cleaned or swabbed before connecting the male luer to maintain aseptic conditions.

As the male luer is inserted against the first end 46 of the valve member 16, the valve member 16 moves in the direction of arrow "A". During such movement, the first pointed end 62 of the cannula 18 is forced through the head portion 50 of the valve member 16 forming an opening 76 therethrough while the ring 20 restricts outward expansion of the head portion 50 and provides compression of the head portion 50 between the ring 20 and the cannula 18.

Furthermore, during such movement the main body portion 52 of the valve member 16 is compressed between ribs 56 as illustrated in FIG. 2 to provide the desired spring force to the valve member 16. Upon full insertion of the male luer and locking engagement of the luer to the housing 14, the opening or openings 70 in the cannula 18 extend to the exterior of the first end 46 of the valve member 16 for communication with the flow path of the male luer.

The syringe can then be activated to discharge the medicament into and through the valve member 16 by the passage 68 of cannula 18 to the male connector portion 28. Once the syringe is empty, the male luer can be disconnected from the female connector portion 25 which automatically returns the valve member 16 to the closed position by the spring bias provided by the longitudinal compression of the valve member 16.

At the same time, the opening 76 in the valve member 16 is positively sealed by the spring bias created by the compression of the head portion 50 between the ring 20 and cannula 18. Thus, a positive mechanical seal is provided to the valve member 16 which prevents leakage and reduces contamination.

Figure 3:
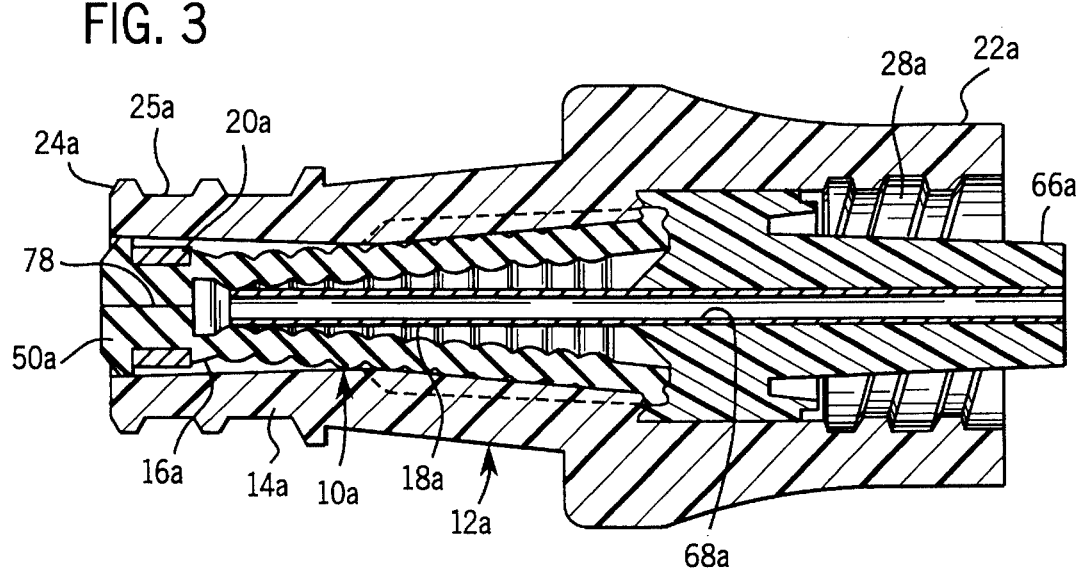
FIG. 3 is a longitudinal cross-sectional view of another embodiment of a valve of the invention illustrated in its closed position within a housing of a medical component for use with a blunt cannula.
Figure 4:
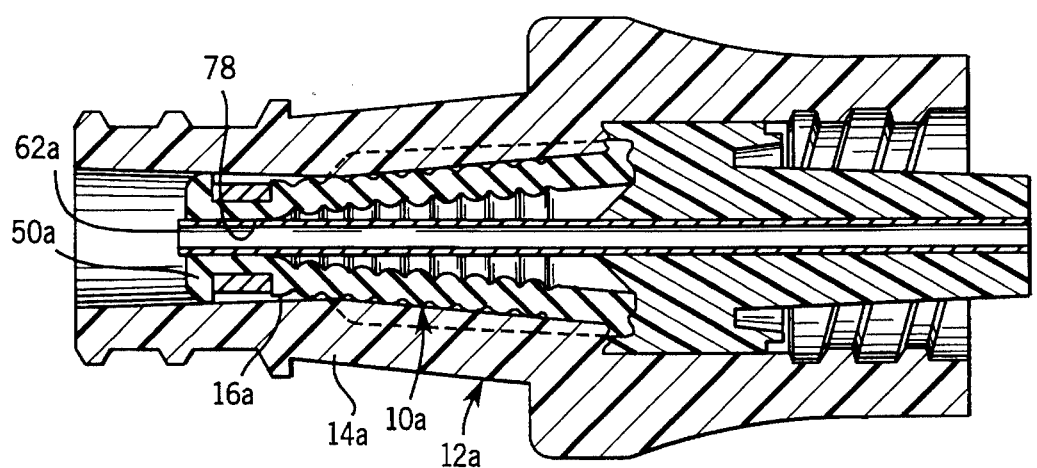
FIG. 4 is a longitudinal cross-sectional view of the valve and housing of FIG. 3 illustrating the valve in its open position.

FIGS. 3 and 4 illustrate another embodiment of the valve of the present invention where similar elements are identified with the same reference numerals including a subscript "a". In this embodiment, the cannula 18a is a blunt cannula and the head portion 50a of the valve member 16a includes a precut slit 78 for insertion of the cannula 18a therethrough.

The remaining elements and operation of this embodiment of the valve 10a are similar to the embodiment of FIGS. 1 and 2.

Figure 5:
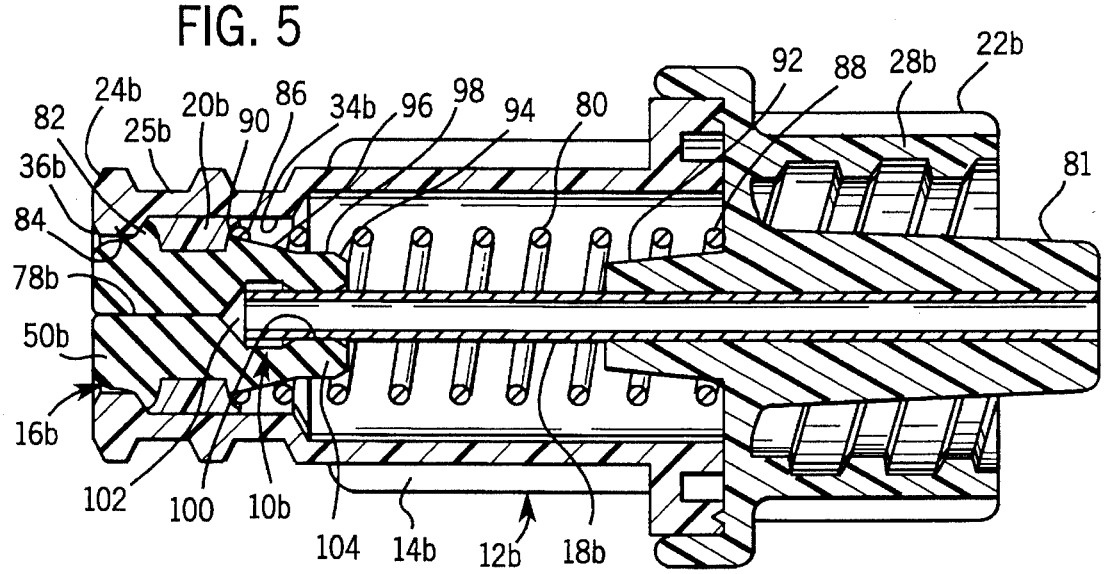
FIG. 5 is a longitudinal cross-sectional view of another embodiment of a valve of the invention illustrated in its closed position within a housing of a medical component for use with a blunt cannula.
Figure 6:
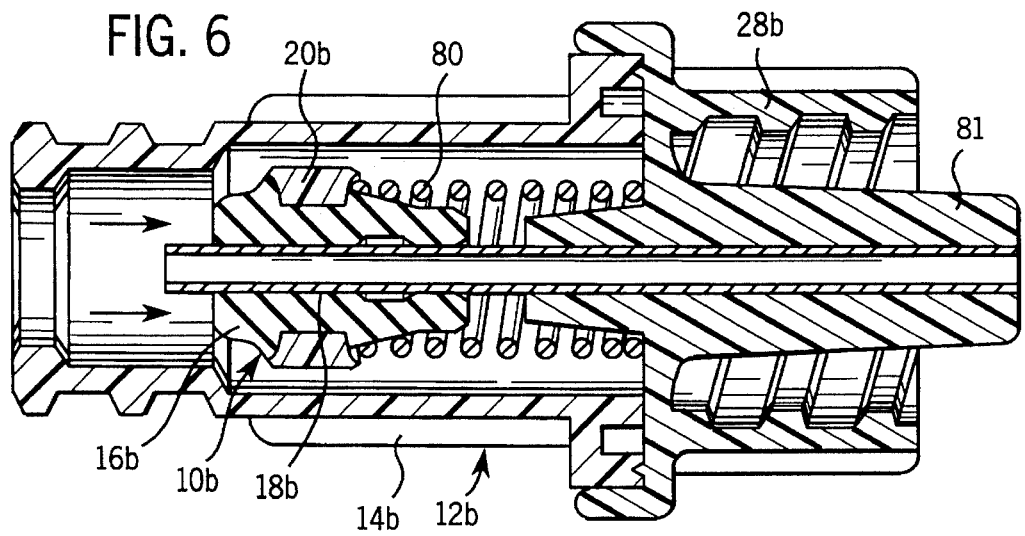
FIG. 6 is a longitudinal cross-sectional view of the valve and housing of FIG. 5 illustrating the valve in its open position.

FIGS. 5 and 6 illustrate another embodiment of the valve of the present invention where similar elements are identified with the same reference numerals including a subscript "b". In this embodiment the valve member 16b is modified, the cannula 18b is blunt, the head portion 50b includes the precut slit 78b and a helical spring 80 is included to substantially replace the main body portion 52 of the valve member 16b.

Additionally, the threaded male connector portion 28b is formed separately from the housing 14b and is secured to the housing 14b and the cannula 18b such as by welding, sonic welding or the like. The threaded male connector portion 28b includes a central tapered engagement column 81 for connection to a patient through an I.V. set tubing or the like.

To prevent the valve member 16b from being ejected from the housing 14b by the force of the spring 80 in the first closed position of the valve member 16b, the valve member 16b includes an engagement portion 82. The engagement portion 82 contacts a collar 84 formed about the interior of the cylindrical portion 34b of the housing 14b proximate the first outside end 36b of the cylindrical portion 34b.

The spring 80 includes first and second opposite ends 86 and 88. The first end 86 is seated within a recess 90 formed with the head portion 50b while the second end 88 is seated about a conical portion 92 formed with the male connector portion 28b.

The head portion 50b also includes a tapered engagement shoulder 94 which is accepted within the confines of the first end 86 of the spring 80. The shoulder 94 is tapered from a first end 96 proximate the head portion 50b to a second end 98 which extends within the spring 80 toward the male connector member 28a.

The head portion 50b also includes a channel 100 having a first interior end 102 which is in communication with the slit 78b and a second exterior end 104 which contacts the cannula 18b. The channel 100 includes an enlarged recess 106 proximate the first interior end 102 which provides a rest position for the cannula 18 which isolates the outward forces which a cannula causes against the valve from the prepierced slot.

The remaining elements and operation of this embodiment are similar to the embodiment of FIGS. 1 and 2 as well as the embodiment of FIGS. 3 and 4.

It will readily be apparent from the foregoing detailed description of the invention and from the illustrations thereof that numerous variations and modifications may be effected without departing from the true spirit and scope of the novel concepts or principles of this invention.

What is claimed is:

1. A valve, comprising:

a substantially rigid cannula;

a generally cylindrical valve member connected for operable communication with said cannula, said valve member being formed from a substantially resilient material and having a solid head portion with an outer periphery and a hollow body portion extending axially from said head portion, said head portion being movable with respect to said cannula between a first closed position and a second open position, said cannula cooperating to extend through said head portion of said valve member during movement from said first closed position to said second open position to establish a fluid flow path through said cannula and said valve member; and sealing means independent from a flow of fluid within said fluid flow path and independent from any component utilized with said valve and circumferentially engaging said outer periphery of the head portion for automatically providing positive sealing of an opening through said head portion of said valve member when said head portion of said valve member is positioned in said first closed position, said cannula extending through said opening during said movement of said valve member, wherein said sealing means moves with said head portion.

2. The valve in accordance with claim 1 wherein said head portion of said valve member includes a preformed slit forming said opening through which said cannula extends.

3. The valve in accordance with claim 2 wherein said cannula is a blunt cannula.

4. The valve in accordance with claim 1 wherein said cannula is pointed and said opening is provided in said head portion of said valve member upon advancement of said cannula therethrough.

5. The valve in accordance with claim 1 including spring means for maintaining said valve member in said first closed position when said valve member is not in use and for automatically returning said vane member to said first closed position from said second open position upon disassembly of said valve member from a fluid delivery system.

6. The valve in accordance with claim 5 wherein said spring means are formed as a portion of said material of said valve member.

7. The valve in accordance with claim 5 wherein said spring means are formed as a separate helical spring.

8. The valve in accordance with claim 1 wherein said valve member includes a portion thereof for activation by a male luer member for providing movement between said first and second positions.

9. A connector for an intravenous fluid line, comprising:

a housing;

a substantially rigid cannula mounted within said housing;

a generally cylindrical valve member positioned within said housing for operable communication with said cannula, said valve member being formed from a substantially resilient material and having a solid head portion with an outer periphery and a hollow body portion extending axially from said head portion, said head portion movable within said housing between a first closed position and a second open position, said cannula extending through said head portion of said valve member during movement of said valve member from said first closed position to said second open position to establish a fluid flow path through said cannula and said valve member; and sealing means independent from a flow of fluid within said flow path and independent from said housing and circumferentially engaging said outer periphery of the head portion for automatically providing positive sealing of an opening through said head portion of said valve member when said valve member is positioned in said first closed position, said cannula extending through said opening during said movement of said valve member wherein said sealing means moves with said head portion.

10. The connector in accordance with claim 9 wherein said head portion of said valve member includes a preformed slit forming said opening through which said cannula extends.

11. The connector in accordance with 10 wherein said cannula is a blunt cannula.

12. The connector in accordance with claim 9 wherein said cannula is pointed and said opening is provided in said head portion of said valve member upon advancement of said cannula therethrough.

13. The connector in accordance with claim 9 including spring means for maintaining said valve member in said first closed position when said valve member is not in use and for automatically returning said valve member to said first closed position from said second open position upon disassembly of said valve member from a fluid delivery system.

14. The connector in accordance with claim 13 wherein said spring means are formed as a portion of said material of said valve member.

15. The connector in accordance with claim 13 wherein said spring means are formed as a separate helical spring.

16. The connector in accordance with claim 9 wherein said valve member includes a portion thereof for activation by a male luer member connected thereto to provide movement between said first and second positions.

17. The connector in accordance with claim 9 wherein at least a portion of said valve member is accessible from the exterior of said housing for cleaning thereof.

18. The connector in accordance with claim 9 wherein said sealing means include an annular engagement member to provide reinforcement of said head portion of said valve member independent from said housing.

19. The connector in accordance with claim 18 wherein said engagement member includes a compression ring positioned about the periphery of said head portion of said valve member which allows for passage of the cannula through the opening while providing a leak-proof seal to the opening upon removal of the cannula.

* * * * *

UNITED STATES PATENT AND TRADEMARK OFFICE
CERTIFICATE OF CORRECTION

PATENT NO. : 5,549,566
DATED : August 27, 1996
INVENTOR(S) : A. M. Elias, et. al.

It is certified that error appears in the above-indentified patent and that said Letters Patent is hereby corrected as shown below:

Column 7, line 53, change "vane" to --valve--.

Column 8, line 56, change "include" to --includes--.

Signed and Sealed this

Eleventh Day of February, 1997

Attest:

BRUCE LEHMAN

Attesting Officer         Commissioner of Patents and Trademarks